(12) United States Patent
Johnston et al.

(10) Patent No.: US 6,372,954 B1
(45) Date of Patent: *Apr. 16, 2002

(54) LIQUID MANAGEMENT MEMBER FOR ABSORBENT ARTICLES

(75) Inventors: Raymond P. Johnston, Lake Elmo; Leigh E. Wood, Woodbury; Allen L. Noreen, Lake Elmo, all of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/467,438

(22) Filed: Jun. 6, 1995

Related U.S. Application Data

(60) Division of application No. 08/293,575, filed on Aug. 22, 1993, now Pat. No. 5,514,120, which is a continuation of application No. 07/986,794, filed on Dec. 8, 1992, now abandoned, which is a continuation-in-part of application No. 07/809,311, filed on Dec. 18, 1991, now abandoned.

(51) Int. Cl.[7] .................................................. A61F 13/46
(52) U.S. Cl. ...................... 604/378; 604/378; 604/379; 604/380; 604/384; 604/385.101
(58) Field of Search .................. 604/378, 385.1, 604/385.2, 368, 379, 380, 384, 385.101

(56) References Cited

U.S. PATENT DOCUMENTS

| | | | | |
|---|---|---|---|---|
| 3,929,135 A | * | 12/1975 | Thompson | 128/287 |
| 4,323,069 A | * | 4/1982 | Ahr et al. | 604/384 |
| 4,414,255 A | | 11/1983 | Tokuyama et al. | 428/156 |
| 4,676,786 A | * | 6/1987 | Nishino | 604/378 |
| 4,735,624 A | * | 4/1988 | Mazars | 604/378 |
| 4,735,843 A | * | 4/1988 | Noda | 428/137 |
| 4,840,692 A | * | 6/1989 | Kamstrup-Larsen | 156/252 |
| 5,514,120 A | | 5/1996 | Johnston et al. | 604/604 |
| 5,728,446 A | | 3/1998 | Johnston et al. | 428/428 |

FOREIGN PATENT DOCUMENTS

| | | |
|---|---|---|
| EP | 0 117 351 A2 | 5/1984 |
| EP | 0 178 108 A2 | 4/1986 |
| EP | 0 301 599 A2 | 1/1989 |
| WO | 9111161 * | 8/1991 |
| WO | WO91/12949 * | 9/1991 ........... B29C/47/12 |
| WO | WO 96/07384 | 3/1996 |

* cited by examiner

*Primary Examiner*—Glenn K. Dawson
*Assistant Examiner*—Michael Bogart

(57) ABSTRACT

Absorbent article comprising an optional liquid permeable topsheet, an optional, sometimes liquid impermeable, backsheet, an absorbent core disposed between the topsheet and backsheet, if any, and at least one liquid management member which comprises a film having at least one microstructure-bearing hydrophilic surface that promotes rapid directional spreading of liquids, the liquid management member and core being in contact.

Also, liquid management members which comprise a film having at least one microstructure-bearing hydrophilic surface that promotes directional spreading of liquids. The surface has a plurality of V-shaped grooves having an angular width of Alpha, Alpha being between about 10° and about 120°. The hydrophilic surface has a contact angle with water of Theta, Theta being equal to or less than (90°–Alpha/2).

15 Claims, 4 Drawing Sheets

LIQUID MANAGEMENT MEMBER FOR ABSORBENT ARTICLES

CROSS-REFERENCE TO RELATED APPLICATIONS

This application is a division of U.S. application Ser. No. 08/293,575, filed Aug. 22, 1993, now U.S. Pat. No. 5,514,120 which is a continuation of U.S. application Ser. No. 07/986,794, filed Dec. 8, 1992, now abandoned, which is a continuation-in-part of application Ser. No. 07/809,311, filed Dec. 18, 1991 now abandoned.

FIELD OF INVENTION

The present invention relates to liquid management members for absorbent articles such as meat tray liners, bed pads, baby diapers, sanitary napkins, and adult incontinent pads.

BACKGROUND OF THE INVENTION

Disposable absorbent articles typically comprise three basic components: a liquid permeable topsheet that is located closest to the skin of the wearer when the article is in use, an absorbent core, and a liquid impermeable barrier sheet which is located on the opposite side of the absorbent core. Other components such as fastening tapes, leg and waist elastics, etc. are also commonly used.

The absorbent core receives and retains liquids that pass through the liquid permeable topsheet and typically comprises a batt of wood fluff fibers. Superabsorbent materials, typically in powder form, are often distributed within the absorbent core to enhance its liquid holding capacity and liquid retention properties.

One problem associated with absorbent articles is the inefficient utilization of the total absorptive capacity of the absorbent core material. This is due in part because absorbent articles normally have an elongated rectangular or hourglass shape and the liquid introduction or insult and spreading of liquid is often confined to the central area of the absorbent core.

Another problem associated with absorbent articles is the inability of the absorbent core to absorb liquids rapidly enough when large amounts of liquid are discharged into the absorbent core over short periods of time. This often results in undesirable side leakage.

To improve the liquid acquisition and lateral spreading properties of absorbent articles, many products have utilized a wicking layer of tissue or crepe. This wicking layer can be located between the liquid permeable topsheet and the absorbent core, in the center of the absorbent core, or in the absorbent core in a location closer to the liquid impermeable barrier sheet. However, tissue and crepe tend to promote isotropic spreading of liquids. That is, liquid tends to spread at similar rates in both the lengthwise and width directions of the absorbent article. As a result, in many instances where the core is elongate, the liquid will leak beyond the side edges of the absorbent article before it has an opportunity to spread to the ends of the absorbent core.

Numerous other approaches have been suggested for improving the liquid distribution and absorption properties of absorbent articles. Most of these approaches have involved the use of channels, reservoirs, apertures, etc. that have been introduced into the wood fluff absorbent core or tissue wicking layer by embossing or corrugation techniques. See, for example, U.S. Pat. No. 4,676,786 (Nishino), U.S. Pat. No. 4,678,464 (Holtman), U.S. Pat. No. 4,655,759 (Romans-Hess et al.), and U.S. Pat. No. 5,030,229 (Yang).

U.S. Pat. No. 4,735,624 (Mazars) discloses a disposable diaper comprising an absorbent pad constituted by an absorbent material consisting essentially of hydrophilic fibers joined to one another to form a coherent mass. The pad is narrow in the crotch area and widens out in the front and rear areas of the diaper with branches.

Other approaches have been taken such as the use of nonwoven inserts as flow control zones, as disclosed in U.S. Pat. No. 4,795,453 (Wolfe) and U.S. Pat. No. 4,908,026 (Sukiennik et al.), or the use of a plastic netting material to promote the unidirectional spreading of liquids in absorbent pads, as disclosed in European patent 0 174 152 B1. The use of certain complex shaped fibers, in tow or staple form, that are capable of spontaneously transporting liquid in absorbent articles is disclosed in European patent application 0 391 814 A2 (Phillips et al.).

U.S. Pat. No. 4,798,604 (Carter) discloses a contoured polymeric film which is apertured and contains a pattern of raised areas that may be employed to form the body contacting surface, i.e, topsheet, in absorbent devices.

Despite these previously known technologies, additional improvements to obtain more efficient and speedier absorption by absorbent cores without leaking are desired.

SUMMARY OF INVENTION

The present invention provides liquid management members that facilitate desired anisotropic or directionally dependent distribution of liquids, and absorbent articles that exhibit excellent liquid acquisition and distribution, resulting in greater effective absorption capacity and greater comfort for the wearer.

In brief summary, articles of the invention typically comprise a liquid permeable topsheet, a backsheet, sometimes preferably liquid impermeable, and an absorbent core disposed between the topsheet and backsheet, wherein the article further comprises at least one liquid management member that promotes rapid directional spreading of liquids. The liquid management member is a sheet, typically flexible, having at least one microstructure-bearing hydrophilic surface with a plurality of channels therein. When an absorbent article is assembled, the hydrophilic surface is in contact with the absorbent core. In some embodiments, the liquid management member is preferably impermeable, i.e., although its surface is hydrophilic the member does not transmit fluid through its body from one surface to the other surface in undesirable fashion. In some embodiments, the liquid management member (which may be impermeable or not as desired) has one or more apertures therein to permit controlled transmission of fluid therethrough in desired manner.

In some embodiments, absorbent articles of the invention may comprise an absorbent mass and at least one liquid management member as described herein, and optionally an attachment member such as a layer of adhesive or a component of a hook and loop fastening system on at least one side.

Articles of the invention may be made in the form of meat tray liners, bed pads, diapers, adult incontinent devices, and feminine hygiene products.

BRIEF DESCRIPTION OF DRAWING

The invention will be further explained with reference to the drawing, wherein.

These figures, which are idealized, are not to scale and are intended to be merely illustrative and non-limiting.

DETAILED DESCRIPTION OF ILLUSTRATIVE EMBODIMENTS

Figure 1:
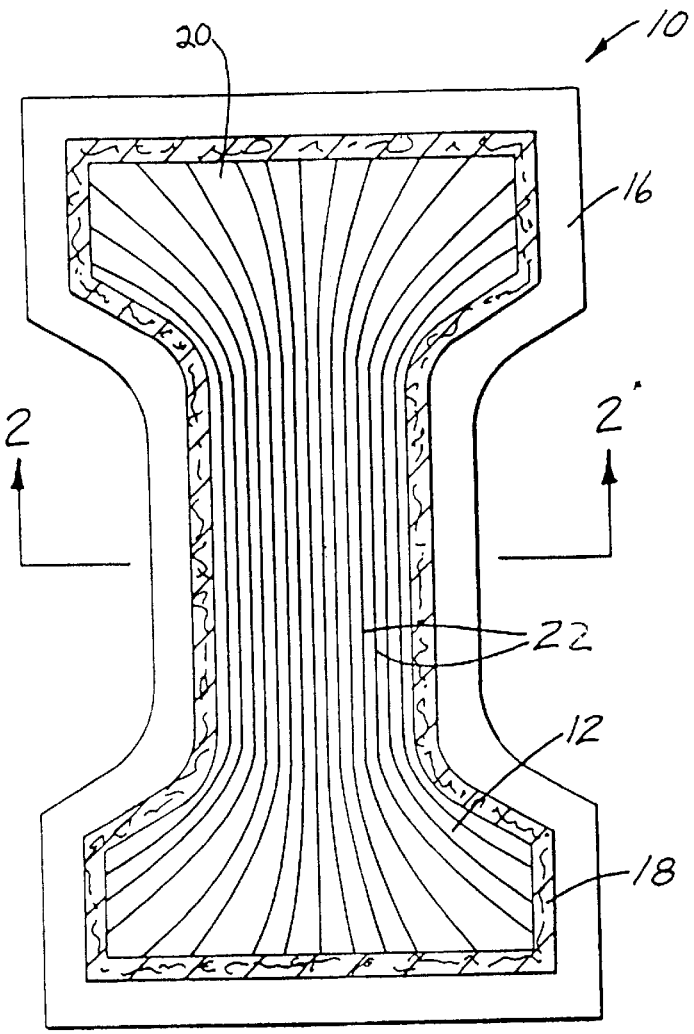
FIG. 1 is a cut-away illustration of one embodiment of a diaper of the invention.
Figure 2:
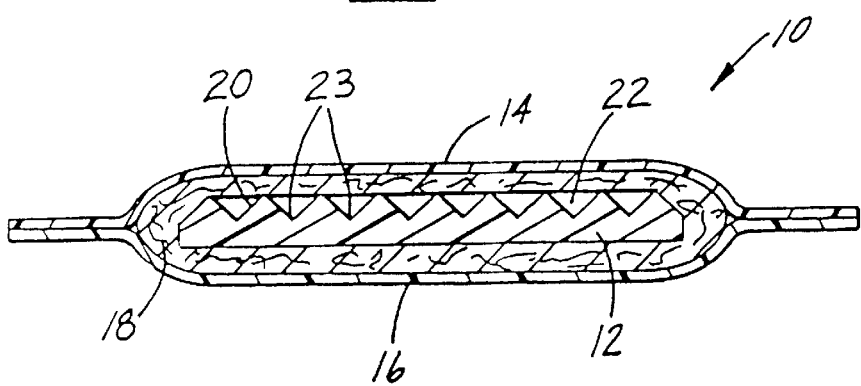
FIG. 2 is a cross-sectional illustration of the diaper of FIG. 1.

FIGS. 1 and 2 show one embodiment of a diaper 10 of the invention comprising liquid management member 12. Diaper 10 also comprises liquid permeable top sheet 14, liquid impermeable backsheet 16, and absorbent core 18. Liquid management member 12 has at least one microstructured hydrophilic surface 20 which promotes anisotropic, and preferably rapid, spreading of liquids in desired direction(s).

The microstructures are channels 22 in the surface of member 12. Typically they are substantially parallel and linear over at least a portion of their length. Liquid management members can be easily formed from thermoplastic materials by casting, profile extrusion, or embossing, preferably by casting or embossing.

Liquid management members of the invention are in the form of sheets or films rather than a mass of fibers. The channels of liquid management members of the invention provide more effective fluid flow than is achieved with webs formed from aggregation of fibers. The walls of channels formed in webs of fibers will exhibit undulations and complex surfaces that interfere with flow of liquid through the channels.

Liquid management members of the present invention are capable of spontaneously transporting liquids along the axis of their channels. Two factors that influence the ability of liquid management members to spontaneously transport liquids (e.g., urine and vaginal secretions) are: 1) the geometry of the surface (capillarity, shape of the channels), and 2) the nature of the film surface (e.g., surface energy).

Figure 3:
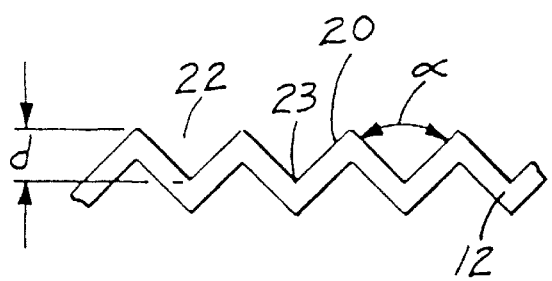
FIGS. 3 and 4 are elevation views of illustrative embodiments of liquid management members of the invention.

The channels of liquid management members of the present invention can be of any geometry that provides desired liquid transport, and preferably one which is readily replicated. With reference to FIG. 3, one preferred geometry is a V-groove 22. The angular width or included angle of the V-groove (i.e., angle Alpha) can be from about 10° to about 120°, preferably from about 10° to about 90°, and most preferably from about 20° to about 60°. It has been observed that channels with narrower angular width provide greater vertical wicking distance. However, if Alpha is too narrow, the wicking action will be too slow to provide liquid transport that is as fast as desired. If Alpha is too wide, the groove may fail to provide desired wicking action. It has been observed that as Alpha gets narrower, the contact angle of the liquid need not be as low to get similar liquid transport as the contact angle must be for grooves with higher angular widths. The depth of the grooves (the height of the peaks above the valleys), "d", is typically substantially uniform, and is typically from about 5 to about 3000 microns, preferably from about 100 to about 1500 microns, and most preferably is from about 200 to about 1000 microns. It will be understood that in some embodiments members with grooves having depths larger than the indicated ranges may be used. If the grooves are too shallow, the wicking action may not result in fast enough movement of desired quantities of fluid. If the grooves are unduly deep, the overall thickness of the liquid management member will be unnecessarily high and the member may tend to be stiffer than is desired.

When used in absorbent articles it is typically preferred that the liquid management members be thin and flexible to avoid imparting undesirable stiffness to the absorbent articles. For instance, in the case of liquid management members used in infant diapers or adult incontinent devices, the thickness typically ranges from about 10 to about 1500 microns, preferably from about 125 to about 1000 microns. The liquid management member should be sufficiently thick to retain its structural integrity when subjected to stresses (e.g., stretching and flexing) expected to be encountered during use. In the case of bed pads, the absorbent article need not be as highly flexible to provide comfort and the liquid management member may be up to 3000 microns or more thick.

Liquid management members can be formed from any thermoplastic materials suitable for casting, profile extrusion, or embossing including, for example, polyolefins, polyesters, polyamides, poly(vinyl chloride), etc. Polyolefins are preferred, particularly polyethylene or polypropylene, blends and/or copolymers thereof, and copolymers of propylene and/or ethylene with minor proportions of other monomers, such as ethylene/vinyl acetate. Polyolefins are preferred because of their excellent physical properties, ease of processing, and typically lower cost than other thermoplastic materials having similar characteristics. Polyolefins readily replicate the surface of a casting or embossing roll and are also readily profile extruded. They are tough, durable and hold their shape well, thus making such films easy to handle after the casting or embossing process. A particularly preferred polyolefin for use in the present invention is TENITE™ 1550P Polyethylene, a low density polyethylene from Eastman Chemical Company, having a melt flow index of 3.5 grams/10 minutes (ASTM D1238) at 190° C. and a density of 0.918 (ASTM D1505). Alternatively, liquid management members can be cast from curable resin materials such as acrylates or epoxies, and cured by exposure to heat or UV or E-beam radiation. Preferably, the liquid management member substantially retains its geometry and surface characteristics upon exposure to liquids.

Figure 7A:
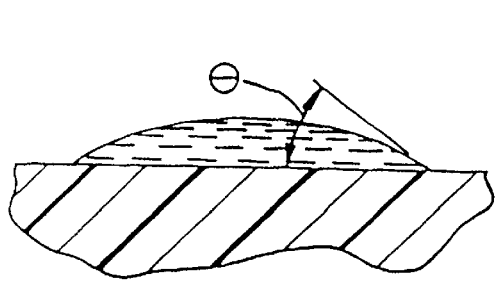
FIGS. 7a and 7b are schematic diagrams used to illustrate interaction of a liquid on a surface.
Figure 7B:
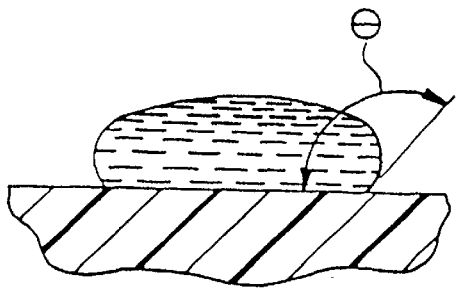

Generally, the susceptibility of a solid surface to be wet out by a liquid is characterized by the contact angle that the liquid makes with the solid surface after being deposited on the horizontally disposed surface and allowed to stabilize thereon. It is sometimes referred to as the "static equilibrium contact angle", sometimes referred to herein merely as "contact angle". As shown in FIGS. 7a and 7b, the contact angle Theta is the angle between a line tangent to the surface of a bead of liquid on a surface at its point of contact to the surface and the plane of the surface. A bead of liquid whose tangent was perpendicular to the plane of the surface would have a contact angle of 90°. Typically, if the contact angle is 90° or less, as shown in FIG. 7a, the solid surface is considered to be wet by the liquid. Surfaces on which drops of water or aqueous solutions exhibit a contact angle of less than 90° are commonly referred to as "hydrophilic". As used herein, "hydrophilic" is used only to refer to the surface characteristics of a material, i.e., that it is wet by aqueous solutions, and does not express whether or not the material absorbs aqueous solutions. Accordingly, a material may be referred to as hydrophilic whether or not a sheet of the material is impermeable or permeable to aqueous solutions. Thus, hydrophilic films used in liquid management members of the invention may be formed from films prepared from resin materials that are inherently hydrophilic, such as for example, poly(vinyl alcohol). Liquids which yield a contact angle of near zero on a surface are considered to completely wet out the surface. Polyolefins, however, are typically inherently hydrophobic, and the contact angle of a polyolefin film, such as polyethylene or polypropylene, with water is typically greater than 90°, such as shown in FIG. 7b. Body liquids that will come into contact with the liquid management members of the present invention are aqueous. Thus, if such films are used as liquid management members of the invention, they must be modified, e.g., by surface treatment, application of surface coatings, or incorporation of selected agents, such that the surface is rendered hydrophilic so as to exhibit a contact angle of 90° or less, thereby enhancing the wetting and liquid transport properties of the liquid management member.

In liquid management members of the invention having V-grooves, the desired surface energy of the microstructured surface of the liquid management member is such that Theta≦(90°−Alpha/2), wherein Theta is the contact angle of the liquid with the member and Alpha is the angular width of the groove.

Any suitable known method may be utilized to achieve a hydrophilic surface on liquid management members of the present invention. Surface treatments may be employed such as topical application of a surfactant, plasma treatment, grafting hydrophilic moieties onto the film surface, sol-gel coating, corona or flame treatment, etc. Alternatively, a surfactant or other suitable agent may be blended with the resin as an internal additive at the time of film extrusion. It is typically preferred to incorporate a surfactant in the polymeric composition from which the liquid management member is made rather than rely upon topical application of a surfactant coating. Topically applied coatings tend to fill in, i.e., blunt, the notches of the channels, thereby interfering with the desired liquid flow to which the invention is directed. An illustrative example of a surfactant that can be incorporated in polyethylene liquid management members is TRITON™ X-100, an octylphenoxypolyethoxyethanol nonionic surfactant, e.g., used at between about 0.1 and 0.5 weight percent. An illustrative method for surface modification of the members of the present invention is the topical application of a 1 percent aqueous solution of the reaction product comprising 90 weight percent or more of:

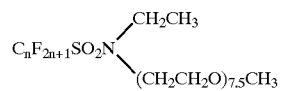

wherein n=8 (97 percent), n=7 (3 percent), and 10 weight percent or less of:

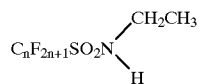

wherein n=8 (97 percent), n=7 (3 percent). Preparation of such agents is disclosed in U.S. Pat. No. 2,915,554 (Ahlbrecht et al.)

Figure 4:
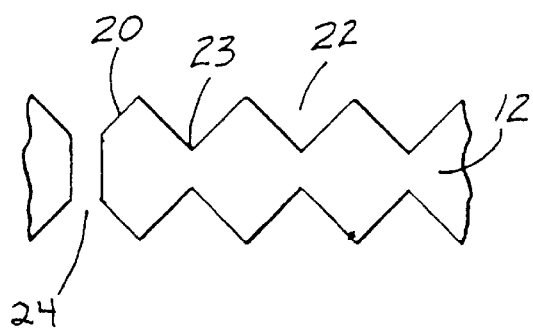

In some embodiments, liquid management member 12 will have channels on only one major surface as shown in FIG. 2. In other embodiments, however, liquid management member 12 will have channels on both major surfaces, as shown in FIGS. 3 and 4. Typically in the case of absorbent articles such as diapers, if the member has channels on both major surfaces, the channels on one surface are substantially parallel to those on the other surface. The channels may be laterally offset from one surface to the other surface as shown in FIG. 3 or may be aligned directly opposite each other as shown in FIG. 4. A liquid management member with offset channels as shown in FIG. 3 provides a maximum amount of surface area for wicking while at the same time using a minimum amount of material. In addition, a liquid management member with offset channels can be made so as to feel softer due to the reduced thickness and boardiness of the sheet than a liquid management member with aligned channels as shown in FIG. 4. As shown in FIG. 4, liquid management members 12 of the invention may have one or more apertures 24 therein which enable a portion of the liquid in contact with the front surface of the liquid management member to be transported to the back surface of the member to improve the control thereof in accordance with the invention. The apertures need not be aligned with the notch of a channel and do not need to be of about equal width as the channels. The surfaces of the liquid management member within the apertures is preferably hydrophilic.

Figure 5:
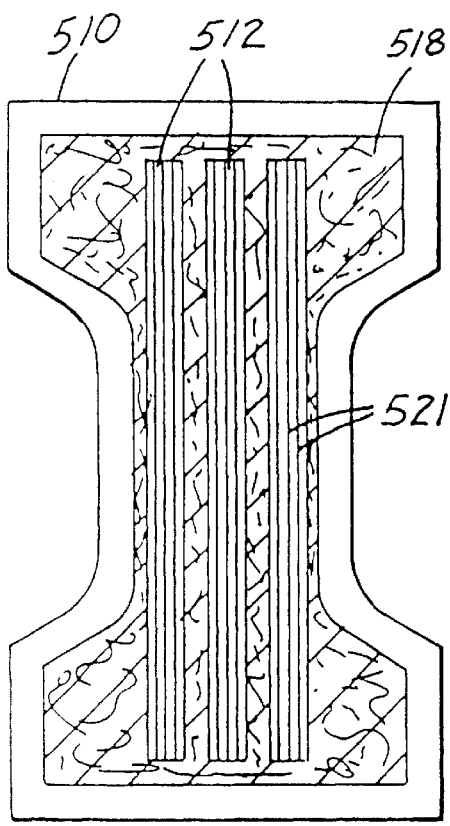
FIGS. 5 and 6 are cut-away illustrations of two other embodiments of diapers of the invention.
Figure 6:
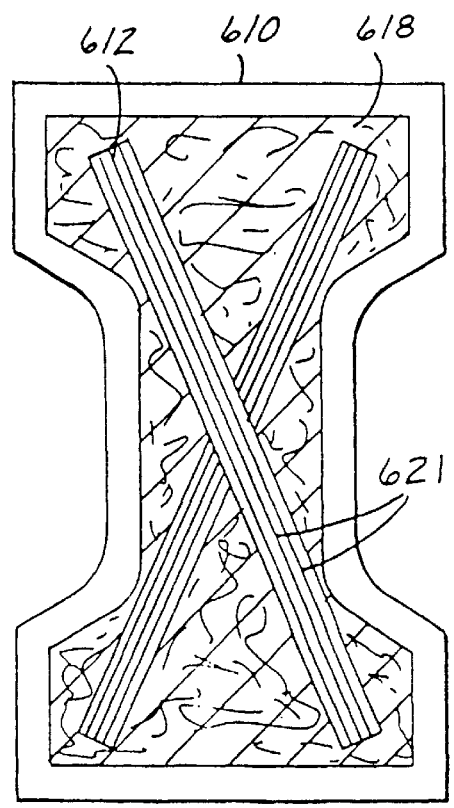

Liquid management member 12 can be incorporated into disposable absorbent article 10 in a number of ways. The member can be cut into one or more generally longitudinal strips that can be placed above, below, or within the absorbent core in a variety of configurations. Several illustrative embodiments are depicted in FIGS. 1, 5, and 6. Diaper 510 in FIG. 5 has three liquid management members 512 with channels 521 arranged in parallel strips in absorbent core 518. Diaper 610 in FIG. 6 has two liquid management members 612 overlaid in an intersecting or "X" pattern in absorbent core 618. Typically, the intersection will be located where liquid introduction is expected.

Figure 12:
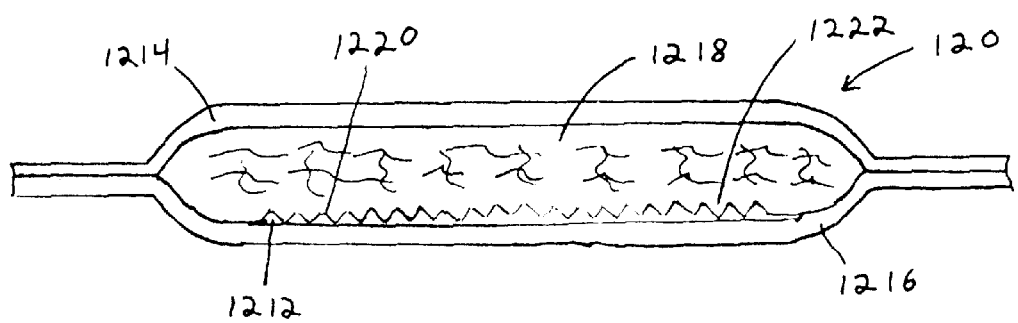
FIG. 12 is a cross-sectional illustration of another embodiment of a diaper of the invention.

If desired, the liquid management member may be disposed on the interior surface of the backsheet or even made integral therewith by forming the desired microstructured surface on the interior surface thereof. In this embodiment, the microstructured film serves two functions, as a liquid transport layer adjacent to the underside of the absorbent core and as a liquid barrier layer for the absorbent article. FIG. 12 illustrates diaper 120 of the invention comprising liquid permeable topsheet 1214, liquid impermeable backsheet 1216, and absorbent core 1218. Liquid management member 1212, with microstructured surface 1220 with grooves 1222, is disposed on the interior surface of backsheet 1216. If desired, grooves 1222 may be formed on the surface of backsheet 1216 such that the liquid management member and backsheet are of unitary construction.

Figure 8:
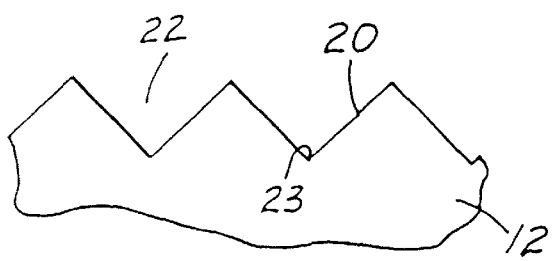
FIG. 8 is a cross-sectional illustration of a portion of a film with channels therein.
Figure 9:
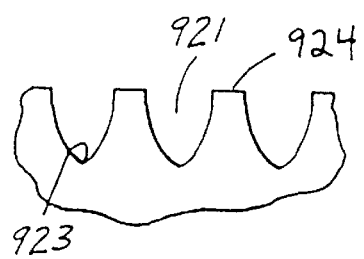
FIG. 9 is a cross-sectional illustration of a portion of a film with channels having a different cross-sectional profile therein.
Figure 10:
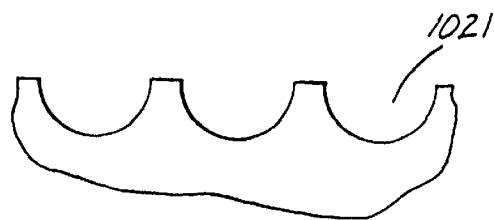
FIG. 10 is a cross-sectional illustration of a portion of a film with channels having a different cross-sectional profile therein.
Figure 11:
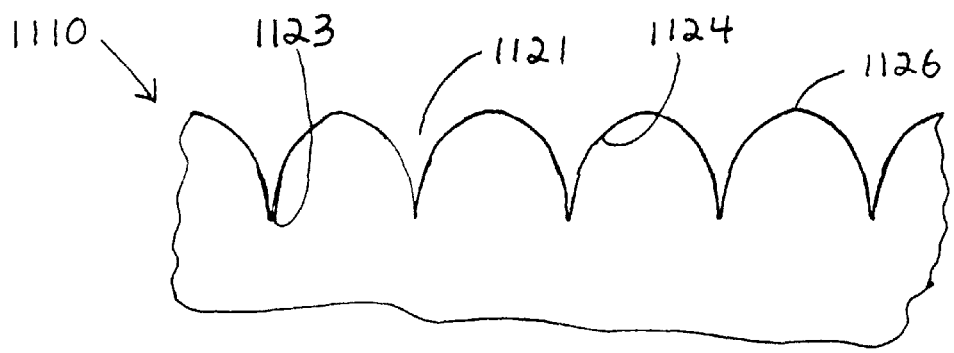
FIG. 11 is a cross-sectional illustration of a portion of a film with channels having a different cross-sectional profile therein.

As mentioned above, a preferred microstructure is one in which the channels are V-shaped grooves, i.e., each channel is defined by a pair of planar walls which meet at a line of intersection. Such channels are easily formed and provide rapid liquid transport. In other embodiments, the sides of the channel need not be planar but the channel preferably possesses a notch that extends parallel to the longitudinal axis of the channel. In other words, when viewed in cross-section, the line of intersection of a plane perpendicular to the axis of the channel and the walls of the channel preferably passes an abrupt slope change, i.e., a geometric discontinuity or a point where the first order derivative of the surface of the channel has multiple values. Although preferred, the notch need not be a perfect V point; typically, useful liquid management is achieved if the notch has a radius of curvature of about 25 microns or less, preferably about 10 microns or less, and more preferably about 5 microns or less. It has been observed that coatings applied to microstructured surfaces to impart desired hydrophilicity thereto may tend to aggregate or pool in the base of the channel, tending to increase the radius of notch. FIG. 8 shows a typical member with V-shaped grooves 22 having notch or abrupt slope change 23, FIG. 9 shows a member with channels 921 having non-planar, inwardly flaring walls and a base with abrupt slope change 923, and FIG. 10 shows a member with channels 1021 having non-planar walls and no abrupt slope change. The liquid management member in FIG. 9 has large crests 924 between adjacent channels 921. It is typically preferred to have narrow crests or, as shown in FIG. 8, closely packed channels such that the walls of adjacent channels are in contact in order to increase the number of channels per unit surface width. FIG. 11 shows a preferred embodiment of liquid management member 1110 of the invention wherein channels 1121 have notch or abrupt slope change 1123 and walls 1124 flare outwardly rather than being straight. For ease of manufacture, the walls between adjacent channels preferably meet at crests 1126 with minimum land area, i.e., a high channel density.

Preferably the channel walls are smooth because an excessive amount of surface roughness will tend to impede desired liquid flow. Liquid management members with channel walls that flare outwardly as shown in FIG. 11 are believed to provide an optimum combination of rapid anisotropic fluid flow and vertical wicking capability and accordingly are preferred for many applications.

Typically, the channels in liquid management members of the invention are oriented in the same direction, i.e., they are substantially parallel throughout their entire length. Channels are considered to be substantially parallel as long as they extend in the same general direction without intersecting; their lateral spacing need not be equal over their entire length.

In a typical absorbent article of the invention as shown in FIG. 1, absorbent core 18 and liquid management member 12 are both elongate and oriented in the same general direction. It is typically preferred that the liquid management member be substantially coextensive with the absorbent core i.e., extend to within about 1 to 2 centimeters of the edge of the absorbent core in most cases. It is also typically preferred that it not extend beyond the absorbent core as this may result in leaking. In such instances, the channels of the liquid management member will typically be oriented along the longitudinal axis of the member and of the absorbent core. Referring again to FIG. 1, it will typically be preferred in such instances for the lateral spacing of channels 22 to vary along their longitudinal axis with the spacing being at a minimum in a longitudinally interior region of member 12 and being wider than the minimum at an exterior region of member 12. Such an article is typically constructed such that the region of minimum lateral spacing is located near expected liquid insult with the wider spacing being located at more distant locations. In such embodiments, liquid management member 12 provides both improved transport of the liquid away from the insult but also improved distribution of the liquid to more distant portions of absorbent core 18. If desired, additional channels (not shown) may begin between the interior region and longitudinal edges of liquid management member 12.

Figure 13:
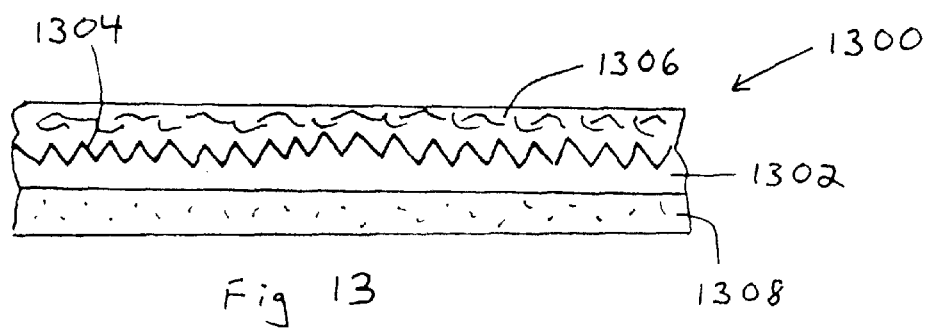
FIG. 13 is a cross-sectional illustration of another embodiment of an absorbent article of the invention.

FIG. 13 shows another embodiment of the invention with absorbent article 1300 comprising liquid management member 1302 with microstructure-bearing surface 1304, absorbent mass 1306, and attachment member 1308 on at least one side. Attachment member 1308 is selected in part based on the substrate to which the absorbent article is to be attached. Illustrative examples include suitable adhesives. Other illustrative examples include a component of a hook and loop fastening system, i.e., a strip of hook material with the strip of loop material being applied to a substrate.

Usually the microstructured surface is in contact with the absorbent core. However, in some embodiments, for instance where the absorbent material is subject to gel blocking, the liquid management member will be oriented such that a microstructure-bearing surface and the absorbent core are disposed on opposite sides of the liquid management member. In such embodiments, the liquid management member is preferably smaller than the absorbent core and/or has apertures therein. In some embodiments, the liquid management member may comprise another microstructure-bearing surface as described herein on the same side as the absorbent core.

Absorbent articles of the invention may be used in a variety of applications. For instance, meat tray liners may be made with liquid management members as described herein. In such embodiments the package is assembled with the topsheet in contact with the meat. The backsheet may be permeable or impermeable.

In simple embodiments, absorbent articles may consist essentially of an absorbent core and liquid management member of the invention.

EXAMPLES

The invention will be further explained by the following illustrative examples which are intended to be nonlimiting.

Unless otherwise indicated, the liquid management members used in the following examples were made from sheets of low density polyethylene, TENITE™ 1550P from Eastman Chemical Company.

Each liquid management member was formed by stamping the sheet with a microstructured nickel tool to form microstructured channels in accordance with invention. The nickel tools were produced by shaping a smooth acrylic surface with diamond scoring tools to produce the desired structure and then electroplating the structure to form a nickel tool with the indicated structure. Unless otherwise indicated, the tools used each provided a group 3.8 centimeters (1.5 inches) wide of a plurality of evenly spaced parallel channels. The tools each had a structured surface with channel forming elements as follows: ribs corresponding in profile to the resultant channels, the crests or tips of the ribs corresponding to the bases or notches in the resultant channels, the creases between adjacent ribs corresponding to the land area between adjacent channels. Unless otherwise indicated, the master tools used had the following features:

| | Tool Features | | | |
|---|---|---|---|---|
| Format | Spacing[1] | Depth[2] | Tip[3] | Angle[4] |
| 1 | 0.240 | 0.33 | NA | 40 ° |
| 2 | 0.520 | 0.33 | NA | 10 °/70 ° |
| 3 | 0.496 | 0.33 | NA | 20 °/60 ° |
| 4 | 0.330 | 0.46 | 2.5 | 40 ° |
| 5 | 0.362 | 0.46 | 25 | 40 ° |

[1]Spacing is the distance between adjacent tips of the tool in millimeters.
[2]Depth is the vertical depth of the channels in millimeters.
[3]Radius of curvature of the tip which forms the notch in the liquid management member in microns.
[4]Angle is the included angle of the ribs in degrees.

In formats 1, 2, and 3 the tips of each rib were defined by the intersection of two planes formed by a diamond scoring tool and the radius is indicated as NA. In formats 4 and 5 the tips were shaped with a diamond scoring tool to have the indicated radius of curvature.

In each of formats 1, 4, and 5 the ribs were of uniform profile. In format 2 ribs having a 10° included angle alternated with ribs having a 70° included angle. In format 3 ribs having a 20° included angle alternated with ribs having a 60° included angle.

The liquid management members formed from each tool are indicated below by identifying the format number from the table above. In some instances, the tool described above was used to from a mirror image tool via electroplating. The mirror image tool was then used to form a liquid management member. In those instances, the liquid management member is indicated by identifying the format number from the table above with a prime "'" notation. For example, a liquid management member formed with tool format 1 will be identified with format number "1" whereas a liquid management member formed with a mirror image tool which was formed from tool format 1 will be identified with format number "1'".

Example 1

Liquid management members were formed according to the method described using other nickel tools to yield V-shaped grooves having the indicated angular width and depth. 0.4 weight percent of polymer grade zinc stearate was included in the polyethylene as a slip agent.

Vertical wicking was measured in accordance with DIN 53924 ("Deutsches Institut Fuer Normung"). The vertical height achieved in 3 minutes by synthetic urine is reported. Horizontal wicking was evaluated by measuring the maximum spread achieved by a 0.037 gram sample of synthetic urine. A liquid comprising:

| Amount (grams) | Component |
|---|---|
| 0.6 | calcium chloride |
| 1.00 | magnesium sulfate |
| 3.30 | sodium chloride |
| 19.40 | urea | in sufficient deionized water to yield 1000 milliliters was used as synthetic urine. This liquid has been determined, using the Wilhelmy Balance Technique, to have a surface tension of about 61 to about 63 dynes/centimeter. A sufficient amount of blue colorant, K7117 D+C Blue No. 1, from H. Kohnstamm and Company, Inc. was added to render the solution dark blue to facilitate observations during testing.

Liquid management members were formed with adjacent (i.e., substantially no land area between neighboring grooves) V-shaped grooves having the indicated angular width and depth. A coating of a solution in deionized water of 1 weight percent of:

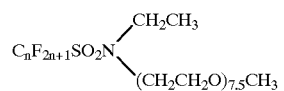

wherein n=8 (97 percent), n=7 (3 percent), and 10 weight percent or less of:

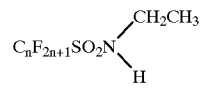

wherein n=8 (97 percent), n=7 (3 percent), was applied to provide a coating thickness (wet) of about 25 microns, and the members were then oven dried at 93° C. (200° F.) for 15 minutes.

The following liquid management results were obtained:

| Groove | | Wicking | |
|---|---|---|---|
| Alpha | Depth[1] | H[2] | V[3] |
| 120 ° | 100 | 11.5 | 0.7 |
| 90 ° | 175 | 15.7 | 1.1 |
| 70 ° | 175 | 15.7 | 2.2 |
| 60 ° | 175 | 17.1 | 4.0 |
| 40 ° | 225 | 16.8 | 6.1 |

[1]In microns.
[2]Horizontal Wicking in centimeters.
[3]Vertical Wicking in centimeters.

Example 2

To assess the relationship of notch sharpness on vertical wicking liquid management members formed from tools 1', 4, and 5 were tested for vertical wicking as in Example 1 except the fluid used was deionized water containing 0.1 weight percent of fluorescent dye, 2-(6-hydroxy-3-oxo-3H-xanthen-9-yl) benzoic acid disodium salt, a fluorescein disodium salt from Eastman Kodak Company. This liquid has been determined, using the Wilhelmy Balance Technique, to have a surface tension of about 74 to 75 dynes/centimeter. The following results were obtained:

| Sample | Format | Radius[1] | Vertical Wicking[2] |
|---|---|---|---|
| 2-1 | 1' | 1.1 | 10.40 |
| 2-2 | 4 | 2.3 | 9.15 |
| 2-2 | 5 | 26. | 5.65 |

[1]Average measured radius of curvature of channel notch in microns.
[2]Vertical height achieved in centimeters.

The notch radius of curvature of the liquid management members were obtained by taking a photomicrograph of the channel cross section with a scanning electron microscope. The polymeric liquid management members were potted in an epoxy which was allowed to cure and then the sample was ground down and polished leaving an exposed cross section of the channel. A photomicrograph of this prepared sample was then taken. Tangent lines were drawn along several points of the tip of the channel. Normal lines to where the tangents contacted the channel were drawn and the location of their intersection identified as the center of curvature of the channel. An average arc radius was then fit to the tip curvature, with the center being the intersection of the normal lines. The arc radius length was then recorded as the radius of curvature reported above.

Example 3

To assess the effects that angular width (Alpha) of the channels and surface properties of the liquid management member (affected by using surfactant) have on vertical wicking distance, vertical wicking tests were performed as in Example 2 using the indicated liquid management members. The vertical wicking results in centimeters were as follows:

| Sample | Alpha | Surfactant (see below) | | | |
| --- | --- | --- | --- | --- | --- |
| | | A | B | C | D |
| 3-1 | 120 | 2.1 | 3.3 | 6.1 | 1.8 |
| 3-2 | 90 | 2.0 | 3.4 | 6.3 | 2.5 |
| 3-3 | 70 | 2.5 | 5.0 | 7.5 | 4.8 |
| 3-4 | 60 | 2.7 | 7.5 | 8.1 | 4.9 |
| 3-5 | 40 | 4.1 | 9.5 | 11.5 | 9.6 |
| 3-6 | 20 | 8.6 | 11.6 | 11.9 | 11.5 |
| 3-7 | 10 | 9.1 | 13.5 | 14.2 | 13.7 |

A A surfactant solution was topically applied as in Example 1.
B 0.1 weight percent of the surfactant solution used in Example 1 was included in the polymer melt.
C 0.5 weight percent of TRITON ™ X-100 was included in the polymer melt.
D 0.5 weight percent of PS071, dimethylsiloxanealkylene oxide copolymer from Patriarch Chemical, was included in the polymer melt.

Tool format 3 was used to make the liquid management member in Sample 3–6. Tool format 2 was used to make the liquid management member in Sample 3–7. The vertical wicking results reported were measured from the channels with the narrow angular width in each Sample.

Various modifications and alterations of this invention will become apparent to those skilled in the art without departing from the scope and spirit of this invention.

What is claimed is:

1. A liquid management member which comprises a film of impermeable material having at least one microstructure-bearing hydrophilic surface that promotes directional spreading of liquids, said surface having a plurality of V-shaped grooves therein, wherein said grooves are spaced apart laterally and the angular width of said grooves is Alpha, said Alpha being between about 10° and about 120°, and said hydrophilic surface has a contact angle with water of Theta, said Theta being equal to or less than (90°−Alpha/2).

2. The article of claim 1 wherein the angular width of said grooves is between about 10° and about 90°.

3. The article of claim 1 wherein the angular width of said grooves is between about 20° and about 60°.

4. The article of claim 1 wherein said grooves are between about 5 and about 3000 microns deep.

5. The article of claim 1 wherein said grooves are between about 100 and about 1500 microns deep.

6. The article of claim 1 wherein said grooves are between about 200 and about 1000 microns deep.

7. The article of claim 1 wherein said liquid management member is impermeable to aqueous liquids.

8. The article of claim 1 wherein said liquid management member has a thickness of between about 125 and 1000 microns.

9. The article of claim 1 wherein said liquid management member has one or more apertures therein.

10. The article of claim 1 wherein said liquid management member is made of one or more polyolefins.

11. The article of claim 1 wherein said grooves are substantially parallel throughout their length.

12. The article of claim 1 wherein said liquid management member is elongate, said grooves are oriented along the longitudinal axis of said liquid management member.

13. The article of claim 1 wherein the lateral spacing of said grooves varies along their longitudinal axis.

14. The article of claim 13 wherein the lateral spacing of said grooves is at a minimum in a longitudinally interior region of said grooves and wherein the lateral spacing of said grooves is wider than said minimum at an exterior region of said grooves.

15. The article of claim 1 wherein said film is flexible.

* * * * *

UNITED STATES PATENT AND TRADEMARK OFFICE
CERTIFICATE OF CORRECTION

PATENT NO. : 6,372,954 B1
DATED : April 16, 2002
INVENTOR(S) : Johnston, Raymond P.

It is certified that error appears in the above-identified patent and that said Letters Patent is hereby corrected as shown below:

<u>Title page,</u>
Item [56], U.S. PATENT DOCUMENTS, the following references should be added:

| | | |
|---|---|---|
| -- 2,915,554 | 12/59 | Ahlbrecht et al. |
| 3,769,978 | 11/73 | DeNight et al. |
| 3,881,490 | 5/75 | Whitehead et al. |
| 4,435,178 | 3/84 | Fitzgerald |
| 4,643,727 | 2/87 | Rosenbaum |
| 4,655,759 | 4/87 | Romans-Hess et al. |
| 4,678,464 | 7/87 | Holtman |
| 4,758,240 | 7/88 | Glassman |
| 4,795,453 | 1/89 | Wolfe |
| 4,798,604 | 1/89 | Carter |
| 4,908,026 | 3/90 | Sukiennik et al. |
| 5,030,229 | 7/91 | Yang |
| 5,037,409 | 8/91 | Chen et al. |

FOREIGN PATENT DOCUMENTS, the following references should be added:

| | | |
|---|---|---|
| 0 174 152 B1 | 3/86 | EPO |
| 0 391 814 | 10/90 | EPO |
| 0 493 728 A1 | 7/92 | EPO |
| 2603491 | 8/77 | DE |
| 8601378 | 3/86 | WO |
| 9109580 | 7/91 | WO |
| 2.082.526 | 12/71 | FR |
| 2 017 505 | 10/79 | GB |
| A 8602543 | 5/86 | WO |
| 28646 | 2/80 | TW |

OTHER PUBLICATIONS, the following references should be added:
ASTM D 1238, Standard Test Method for Flow Rates of Thermoplastics by Extrusion Plastometer
ASTM D 1505, Standard Test Method for Density of Plastics by the Density-Gradient Technique
Herausgeber: Fonds der Chemischen Industrie zur Forderung der Chemie und der Biologischen Chemie im Verband der Chemischen Industrie, "Tenside," KarlstraBe 21, Frankfurt 1, 1987 (English translation provided) --

UNITED STATES PATENT AND TRADEMARK OFFICE
CERTIFICATE OF CORRECTION

PATENT NO. : 6,372,954 B1
DATED : April 16, 2002
INVENTOR(S) : Johnston, Raymond P.

It is certified that error appears in the above-identified patent and that said Letters Patent is hereby corrected as shown below:

Column 7,
Line 14, "passes" should read -- possess --

Column 9,
Line 32, "from" should read -- form --

Signed and Sealed this

Seventeenth Day of June, 2003

JAMES E. ROGAN
*Director of the United States Patent and Trademark Office*